(12) United States Patent
Adams et al.

(10) Patent No.: US 9,283,096 B2
(45) Date of Patent: Mar. 15, 2016

(54) VASCULAR REINFORCEMENT DEVICE

(71) Applicant: Empire Technology Development LLC, Wilmington, DE (US)

(72) Inventors: John Mathew Adams, Snohomish, WA (US); Daniel Hawkins, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/129,864

(22) PCT Filed: Dec. 18, 2012

(86) PCT No.: PCT/US2012/070422
§ 371 (c)(1),
(2) Date: Dec. 27, 2013

(87) PCT Pub. No.: WO2014/098810
PCT Pub. Date: Jun. 26, 2014

(65) Prior Publication Data
US 2015/0157476 A1    Jun. 11, 2015

(51) Int. Cl.
*A61F 2/82* (2013.01)
*A61F 2/00* (2006.01)
(Continued)

(52) U.S. Cl.
CPC .......... *A61F 2/82* (2013.01); *A61F 2/0063* (2013.01); *A61F 2/02* (2013.01); *A61F 2/06* (2013.01); *A61F 2230/0058* (2013.01); *A61F 2230/0095* (2013.01)

(58) Field of Classification Search
CPC .............. A61F 2002/821; A61F 2/064; A61F 2002/065; A61F 2/0063; A61F 2/82
USPC ............. 623/1.15, 1.35, 23.64; 606/151, 153; 600/37
See application file for complete search history.

(56) References Cited

U.S. PATENT DOCUMENTS 3,823,705 A * 7/1974 Trimble .......................... 600/37
6,648,911 B1 * 11/2003 Sirhan et al. ................. 623/1.15
(Continued)

FOREIGN PATENT DOCUMENTS

WO    2009011918 A1    1/2009
WO    2012088069 A2    6/2012

OTHER PUBLICATIONS

International Search Report and Written Opinion for PCT/US12/70422, filed Dec. 18, 2012, mailed on Apr. 11, 2013.
(Continued)

*Primary Examiner* — David Isabella
*Assistant Examiner* — Suba Ganesan
(74) *Attorney, Agent, or Firm* — Turk IP Law, LLC

(57) ABSTRACT

Technologies are generally provided for a vascular reinforcement device for preventing compression of a blood vessel in the presence of applied external forces applied which may occur due to pregnancy and obesity. The vascular reinforcement device may include a first portion configured to be positioned over the aorta and a second portion coupled perpendicularly with the first portion, the second portion configured to be positioned over the left renal vein for preventing the left renal vein from being compressed against the rigid aorta. A reinforcement structure may be embedded into the second portion for providing further protection from compression of the vein passing through the second portion. The vascular reinforcement device may be configured in an initial reduced profile position for delivery to the abdominal area via a delivery tube, and may be deployed into an expanded position over the aorta and the left renal vein.

19 Claims, 7 Drawing Sheets

(51) Int. Cl.
*A61F 2/02* (2006.01)
*A61F 2/06* (2013.01)

(56) References Cited

U.S. PATENT DOCUMENTS

| | | | |
|---|---|---|---|
| 6,743,243 | B1 | 6/2004 | Roy et al. |
| 6,986,751 | B2 * | 1/2006 | Villafana ............... A61F 2/064 604/8 |
| 7,326,240 | B1 * | 2/2008 | Caro et al. ................... 623/1.15 |
| 8,163,005 | B2 | 4/2012 | Lawrence-Brown |
| 2001/0029385 | A1 | 10/2001 | Shennib et al. |
| 2001/0044631 | A1 * | 11/2001 | Akin ...................... A61B 17/11 606/153 |
| 2003/0055486 | A1 | 3/2003 | Adams et al. |
| 2004/0073292 | A1 | 4/2004 | Adams et al. |
| 2006/0069426 | A1 | 3/2006 | Weinberger |
| 2006/0178554 | A1 | 8/2006 | Mandel |
| 2009/0024208 | A1 | 1/2009 | Barker |
| 2010/0070019 | A1 * | 3/2010 | Shalev ......................... 623/1.15 |
| 2010/0292774 | A1 | 11/2010 | Shalev |
| 2011/0213408 | A1 | 9/2011 | Gross et al. |
| 2011/0264116 | A1 | 10/2011 | Kocur et al. |
| 2012/0136385 | A1 | 5/2012 | Cully |

OTHER PUBLICATIONS

Gyselaers, "Hemodynamics of the maternal venous compartment: a new area to explore in obstetric ultrasound imaging", Ultrasound Obstet Gynecol, vol. 32, Issue 5, pp. 716-717, Oct. 2008.

Gyselaers et al., "Maternal renal interlobar vein impedance index is higher in early- than in late-onset pre-eclampsia", Ultrasound Obstet Gynecol, vol. 36, Issue 1, pp. 69-75, Jul. 2010.

Masoura et al., "Neonatal outcomes of late preterm deliveries with preeclampsia", Minerva Gynecology, vol. 64, Issue 2 pp. 109-115, Apr. 2012.

Suggerman, "Hypothesis: preeclampsia is a venous disease secondary to an increased intra- abdominal pressure", Medical Hypotheses, vol. 77, Issue 5, pp. 841-849, Nov. 2011.

Gyselaers et al., "Role of dysfunctional maternal venous hemodynamics in the pathophysiology of preeclampsia: a review", Ultrasound Obstet Gynecol., vol. 38, Issue 2, pp. 123-129 , Aug. 2011.

Bateman et al., "Renal Venous Doppler Sonography in Preeclampsia", J Ultrasound Med., vol. 23, Issue 12, pp. 1607-1611, Dec. 2004.

Tokunaga et al., "Dilatation of the Left Renal Vein in Preeclampsia," J Matern Fetal Med., vol. 9 Issue 6, pp. 356-359, Nov.-Dec. 2000.

Lydakis et al., "The prevalence of preeclampsia and obstetric outcome in pregnancies of normotensive and hypertensive women attending a hospital specialist clinic", Abstract, Int J Clin Pract., vol. 55, Issue 6, pp. 361-367, Jul.-Aug. 2001.

Dalfsen, "Preeclampsia, intra-abdominal pressure and the renal veins", Philica, May 10, 2011, Retrieved from URL : <http://www.philica.com/display_article.php?article_id=240>.

Syed, "Renal Vein Stenting via the Right Internal Jugular Approach With a Provocative Valsalva Maneuver to Reduce the Risk of Stent Migration," Perspective in Vascular Surgery and Endovascular Therapy, vol. 23, Issue 4, Dec. 2011, pp. 268-271.

Russo et al., "Gross hematuria of uncommon origin: the nutcracker syndrome," Am J. Kidney Dis, vol. 32, Issue 3, Sep. 1998, p. E3.

* cited by examiner

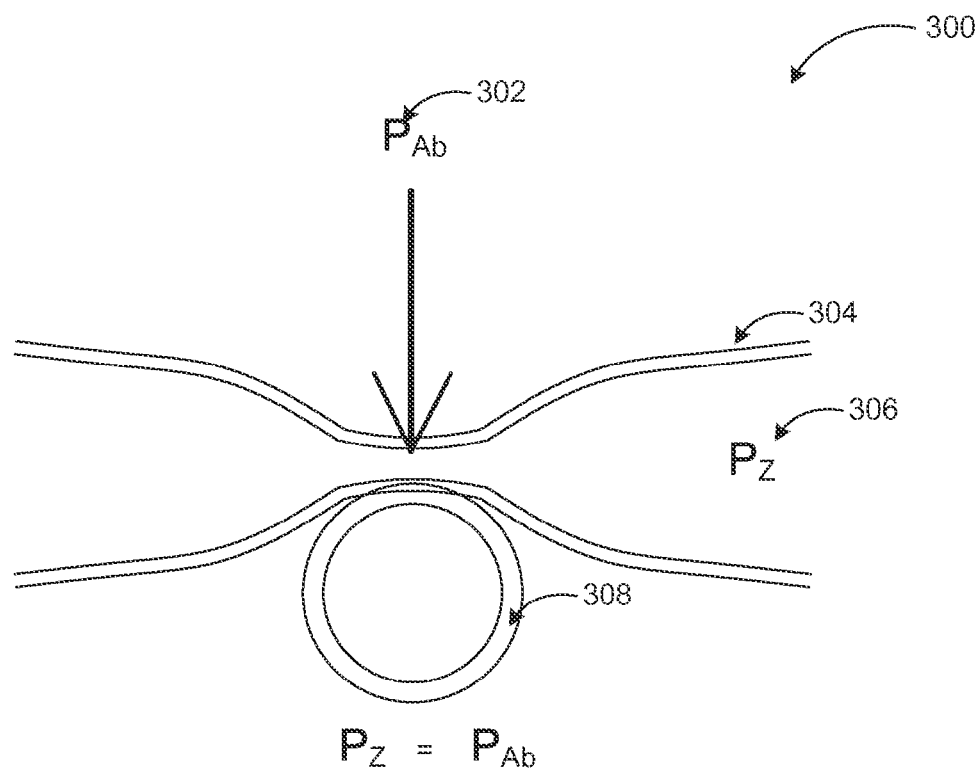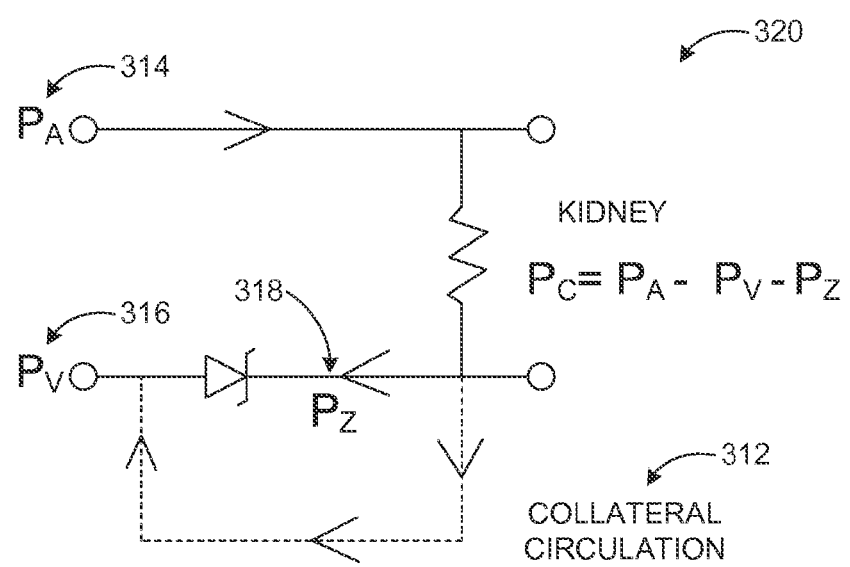
FIG. 3

VASCULAR REINFORCEMENT DEVICE

CROSS-REFERENCE TO RELATED APPLICATION

This application is the National Stage filing under 35 U.S.C §371 of PCT Application Ser. No. PCT/US12/70422 filed on Dec. 18, 2012. The PCT Application is herein incorporated by reference in its entirety.

BACKGROUND

Unless otherwise indicated herein, the materials described in this section are not prior art to the claims in this application and are not admitted to be prior art by inclusion in this section.

Preeclampsia is a pregnancy induced hypertension that can be associated with proteinuria (an excess of serum proteins in the urine) and edema. Preeclampsia typically occurs in 5-10% of pregnancies, and is characterized by symptoms such as swelling, sudden weight gain, headaches and changes in vision. Preeclampsia can progress to eclampsia, with cerebral symptoms leading to convulsions. The condition is associated with systemic vasospasm wherein arteries throughout the body narrow. This can lead to multi-organ system dysfunction wherein many organs of the body, including the kidneys, brain, eyes, liver, etc., are unable to function normally because of altered blood flow and increased blood pressure. Currently the only effective treatment is delivery of the fetus and placenta. Typically, preeclampsia occurs after 20 weeks gestation (in the late 2nd or 3rd trimester), though it can occur earlier.

While the cause of preeclampsia is still being debated, inadequate blood supply to the placenta, abnormalities in the immune system and maternal endothelial cell dysfunction are suspected to be involved. A theorized cause of preeclampsia is compression of the left renal vein due to increased abdominal pressures caused by the growing uterus and abdomen during pregnancy. Abdominal organs can shift due to the growing uterus and can pin the left renal vein, which passes between the vertebra and the aorta, against the rigid aorta causing the blood pressure within the left renal vein to increase substantially. The increase in blood pressure within the left renal vein activates a biological system in the kidney which in effect causes increased system blood pressure, or hypertension. Other circumstances can also trigger the hypertension symptoms, for example, obesity can cause external forces to be exerted on the left renal vein against the aorta, leading to a higher than normal renal vein pressure resulting in hypertension and preeclampsia symptoms.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some examples, the present disclosure describes a vascular reinforcement device for preventing compression of a vein. The vascular reinforcement device includes a first portion having a substantially elongated shape and a hollow interior, the first portion configured to saddle an aorta, and a second portion coupled with the first portion, the second portion having a substantially elongated shape and a hollow interior open and connected to the hollow interior of the first portion, the second portion configured to enable a vein to pass through the hollow interior of the second portion.

According to some examples, the present disclosure describes a method of preventing compression of a vein from external bodily tissue forces. The method may include providing a vascular reinforcement device configured to prevent external pressures from compressing a vein, the vascular reinforcement device including a first portion having a substantially elongated shape and a hollow interior configured to saddle an aorta, and a second portion coupled with the first portion, the second portion having a substantially elongated shape and a hollow interior open and connected to the hollow interior of the first portion, positioning the first portion of the vascular reinforcement device over an aorta, and enabling the vein to pass through the hollow interior of the second portion.

According to some examples, the present disclosure describes a system for preventing compression of a vein from external bodily tissue forces. The system may include a surgical delivery tube for providing percutaneous access to an internal area of a body via at least one incision in the skin of body, and a vascular reinforcement device including a first portion having a substantially elongated shape and a hollow interior configured to saddle an aorta, and a second portion coupled with the first portion, the second portion having a substantially elongated shape and a hollow interior open and connected to the hollow interior of the first portion, wherein the vascular reinforcement device may be configured in an initial reduced profile position for delivery to the internal area of the body via the delivery tube and deployed into an expanded position.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 3 illustrates the location of the left renal vein where it crosses the aorta and a schematic diagram of the blood pressure when the left renal vein is compressed;

DETAILED DESCRIPTION

Figure 1:
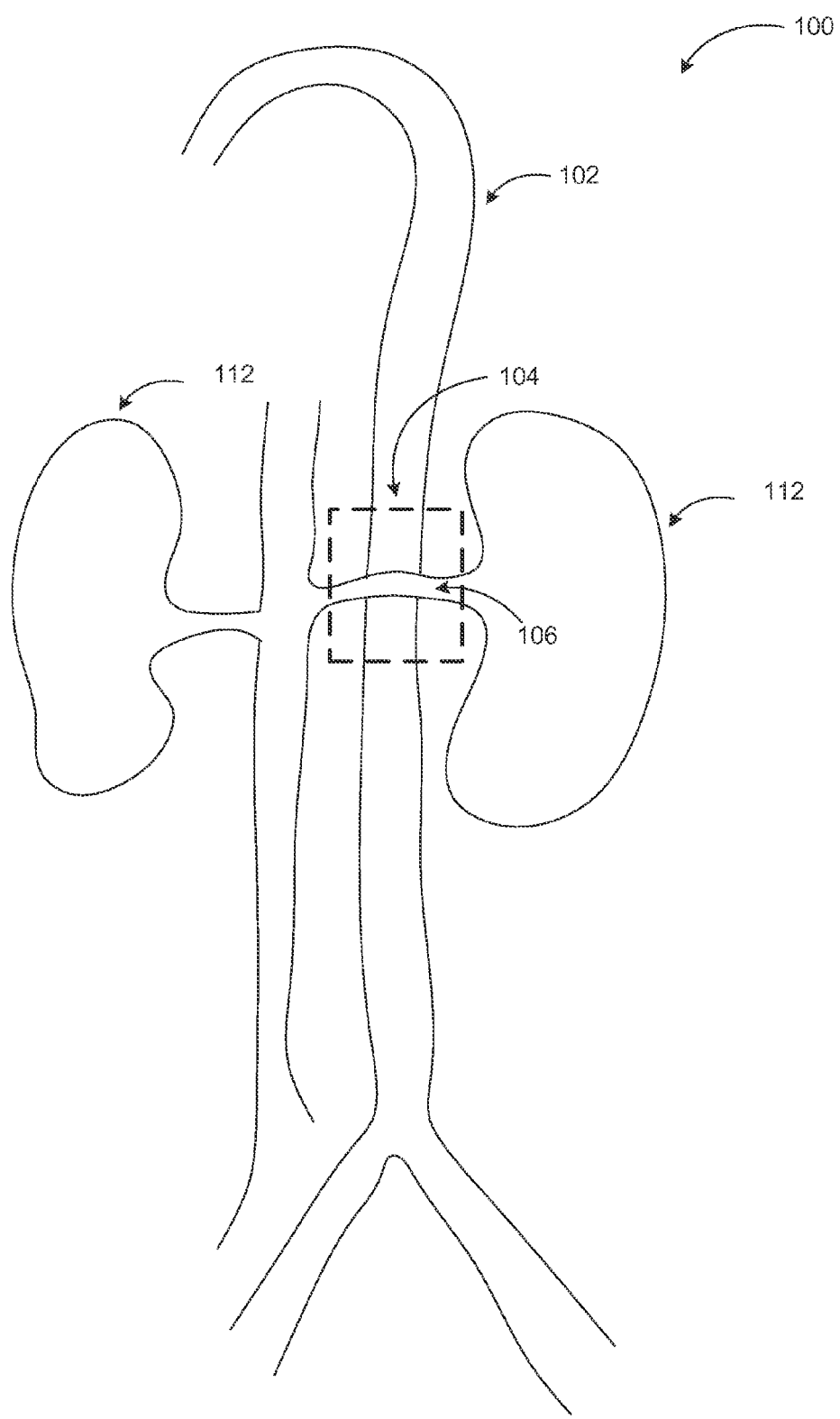
FIG. 1 illustrates an example anatomical layout of the abdomen including the kidneys, left renal vein, inferior vena cava, and the aorta.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to providing avascular reinforcement device for preventing compression of a vein.

Briefly stated, a vascular reinforcement device is provided for preventing compression of a blood vessel in the presence of applied external forces applied which may occur due to pregnancy and obesity. The vascular reinforcement device may include a first portion configured to be positioned over the aorta and a second portion coupled perpendicularly with the first portion, the second portion configured to be positioned over the left renal vein for preventing the left renal vein from being compressed against the rigid aorta. A reinforcement structure may be embedded into the second portion for providing further protection from compression of the vein passing through the second portion. The vascular reinforcement device may be configured in an initial reduced profile position for delivery to the abdominal area via a delivery tube, and may be deployed into an expanded position over the aorta and the left renal vein.

FIG. 1 illustrates an example anatomical layout of the abdomen including the kidneys, left renal vein, inferior vena cava, and the aorta, arranged in accordance with at least some embodiments as described herein. As illustrated in diagram 100, the abdominal cavity includes a right kidney 110, a left kidney 112, inferior vena cava 114, aorta 102, left renal vein 106, and right renal vein 116. The left renal vein 106 connects the left kidney 112 to the inferior vena cava 114 for support blood flow from the left kidney 112 through the inferior vena cava 114 and back to the heart. The left renal vein 106 passes over 104 and is immediately adjacent to the aorta 102. The aorta 102 is a large artery and is at high fluid/blood pressure and has a rigid structure when compared to the compliant vascular structure of a relatively low pressure in the left renal vein 106.

Often times the left renal vein 114 can be subjected to compressive forces within the abdominal area. For example the expansion of tissue and organs in obese persons and the expanding uterus in pregnant persons can cause compression of the left renal vein 114 against the rigid aorta 102 due to increased abdominal pressure and shifting organs. When the left renal vein 114 is compressed against the rigid aorta 102, the left renal vein 114 may distort, such that a diameter of the left renal vein 114 decreases due to the compression against the rigid aorta 102. When the diameter of the left renal vein 114 decreases, the left kidney 112 attempts to maintain a constant blood flow through the left renal vein 114 and the blood pressure within the left renal vein 114 increases on the left side of the aorta, i.e. upstream from the restriction on the left renal vein. The increased blood pressure within the left renal vein 114 is sensed as if it were a reduced aortic pressure by sensors the left kidney 112, as described further in FIG. 3, and in response, the left kidney 112 activates the renin-angiotensin system (RAS). The RAS triggers an increased production of renin enzyme which leads to increased angiotensin II production. Angiotensin II causes the blood vessels within the body to constrict, leading to systemic (whole body) vasospasm and increased systemic blood pressure, known as hypertension and, in pregnancy, as preeclampsia. Additionally, the increased systemic blood pressure leads to aldosterone production which causes water retention in the kidneys, and causes additional decreased kidney perfusion due to vasospasm, which causes the cycle of increased blood pressure regulation to continue.

To further illustrate the sensitivity of the left renal vein 114 to compressive abdominal forces, flow through a vein is equal to the pressure drop from one end of the vein to the other divided by the vascular resistance. In a vein, the vascular resistance is very sensitive to the diameter of the vein. The vascular resistance increases in inverse relation to the fourth power of radial decrease. For example, if the radius is halved, the vein pressure increases by a factor of sixteen in order to maintain constant blood flow through the vein. As a further example, if a vein is normally 6 mm in diameter and the diameter is decreased by 1 mm, the vascular pressure will double to maintain constant flow. Thus a slight compression of the left renal vein causing even a small change in diameter of the left renal vein can cause a substantial pressure increase within the vein to enable the constant flow to be maintained.

Figure 2:
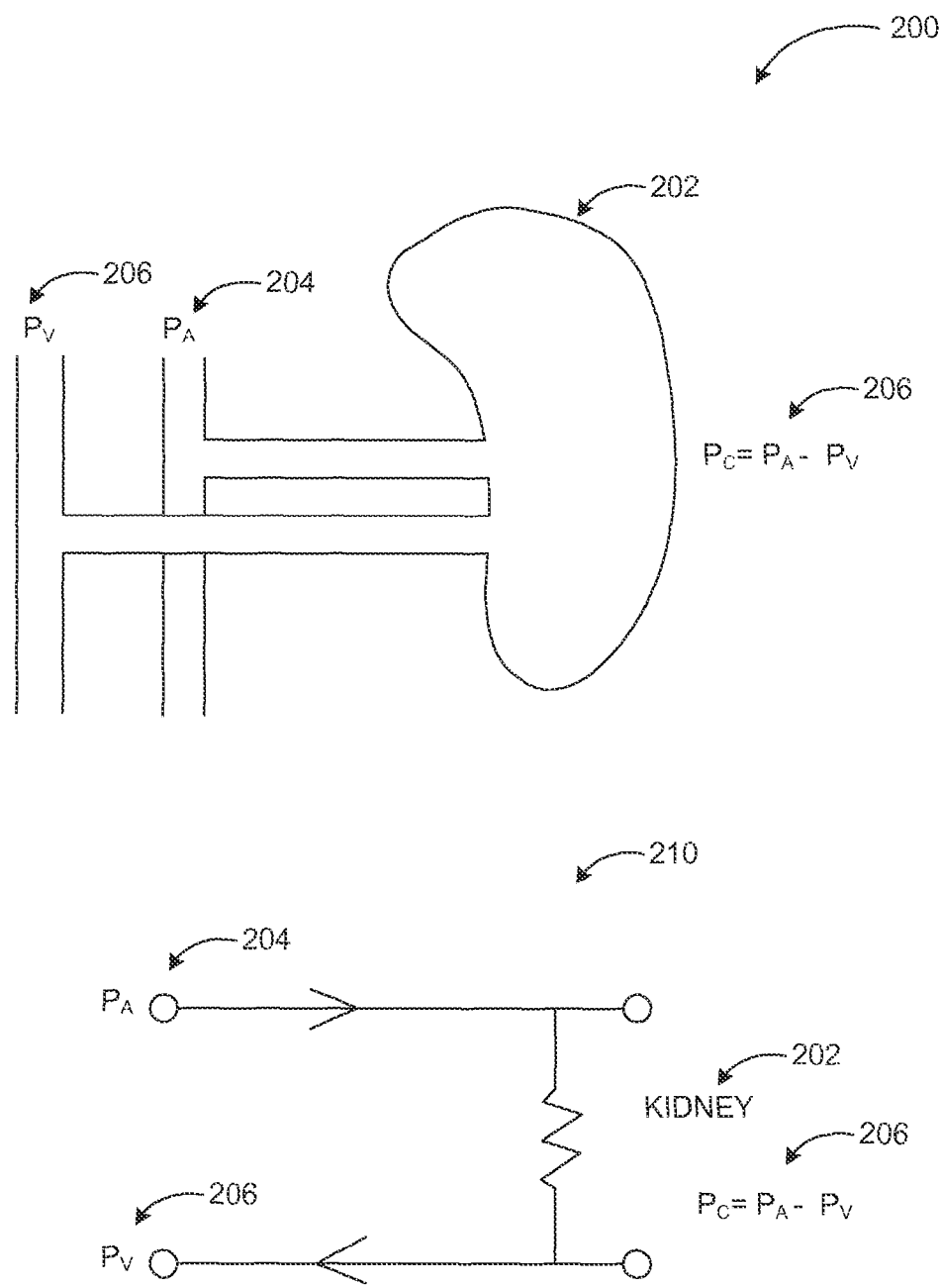
FIG. 2 illustrates an arrangement of the left renal vein and renal artery and a schematic of the corresponding blood pressures.

FIG. 2 illustrates an arrangement of the left renal vein and renal artery and a schematic of the corresponding blood pressures, arranged in accordance with at least some embodiments as described herein. As illustrated in diagram 200, in a typical blood pressure scenario when the left renal vein 208 is not compressed, the left kidney 202 observes the blood pressures in the aorta and the inferior vena cava. The blood pressure $P_c$ 206 the left kidney 202 senses is the difference between the aortic blood pressure $P_A$ 204 and the inferior vena cava blood pressure $P_v$ 206 ($P_c=P_A-P_v$). Diagram 210 is a schematic representation of the blood pressure detected by the left kidney 202. The blood pressure $P_c$ 206 the left kidney 202 sees is the difference between the aortic blood pressure $P_A$ 204 and the inferior vena cava blood pressure $P_v$ 206 ($P_c=P_A-P_v$).

FIG. 3 illustrates the location of the left renal vein where it crosses the aorta and a schematic diagram of the blood pressure when the left renal vein is compressed, arranged in accordance with at least some embodiments as described herein. As illustrated in diagram 300, if there is a pressure point 310 on the left renal vein 304 due to increased abdominal pressure $P_{Ab}$ 302, it can compress the left renal vein 304 against the much harder aorta 308 resulting in a decreased diameter of the left renal vein 304. Pressure $P_z$ 306 is the pressure needed in the left renal vein 304 to compensate for the compressive abdominal pressure $P_{Ab}$ to allow blood to flow past the pressure point 310.

Diagram 310 illustrates a schematic layout of the pressures when there is increased abdominal pressure on the left renal vein 304. The pressure $P_c$ 322 observed by the left kidney is $P_c=P_A-P_z-P_v$. In this case $P_c$ will be less than the case above where there is no compressive force on the LRV. While the aortic pressure $P_A$ is the same in both models, the pressure the left kidney observes during compression of the left renal vein is less than what it should be and the kidney senses a low systematic blood pressure. When the left kidney senses a low systematic blood pressure, the left kidney begins an attempt to correct the low systematic blood pressure it senses by increasing the aortic pressure. Also illustrated in diagram 320 is an alternate collateral circulation return path for venous blood from the left kidney. This alternate or collateral circulation is common in about 85-90% of patients, and passes under the aorta. When the alternate collateral circulation is present, the present $P_z$ will be zero such that the blood pressure $P_c$ 322 observed by the left kidney is returned to $P_c=P_A-P_v$, which represents the systemic blood pressure without pinching of the left renal vein due to increased abdominal pressure.

Figure 4:
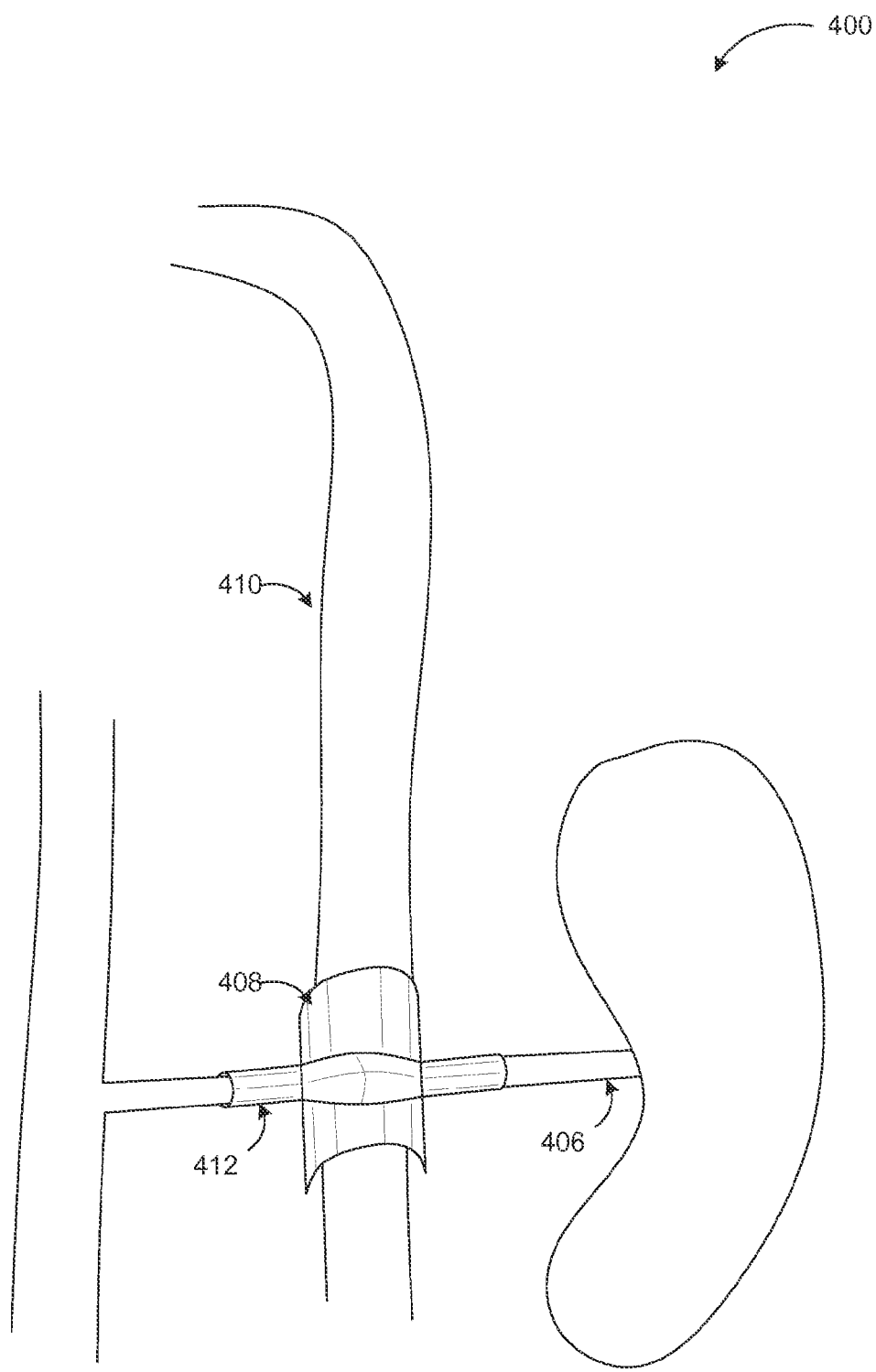
FIG. 4 illustrates a vascular reinforcement device that can be placed over the left renal vein and the aorta for protecting the left renal vein from external pressures.

FIG. 4 illustrates placement of a vascular reinforcement device over the left renal vein where it crosses the aorta, arranged in accordance with at least some embodiments as described herein. As illustrated in diagram 400, the vascular reinforcement device may be positioned over the aorta 410 and the left renal vein 406 for preventing the left renal vein 406 from being compressed against the aorta 410 due to increased abdominal pressures. A first portion 408 of the vascular reinforcement device may be configured to fit over the aorta 410 and a second portion 412 of the vascular reinforcement device may configured to fit over the left renal vein 406 at the position where the aorta 410 crosses the left renal vein 406.

The vascular reinforcement device may be composed of a material such that when the vascular reinforcement device is in position over the aorta 410 and the left renal vein 406, the vascular reinforcement device may prevent compression of the left renal vein 406 against the aorta due to increased pressures within the abdomen. The vascular reinforcement device may be composed of a polymer material, such as polyethylene, polypropylene, polyester, polyurethane, polystyrene, polysulfone and/or polyethersulfone. Additionally, the vascular reinforcement device may be composed of a bio-absorbable material. Some example bio-absorbable materials include polyglycolic acid, polylactic acid, and polydioxanone. The vascular reinforcement device may further be composed of a metal material such as nickel titanium alloy or stainless steel for providing a structure capable of withstanding external pressures exerted on the vascular reinforcement device within the abdomen. In further embodiments, the vascular reinforcement device may be composed from a flexible material enabling the vascular reinforcement device to be collapsible into a reduced profile position for delivery into the body through a delivery tube, and the vascular reinforcement device may include a rigid reinforcement structure for enabling the vascular reinforcement device to resist applied external pressures. The vascular reinforcement device may be configured to resist applied external pressures from about 50 mmHg to about 100 mmHg.

Figure 5:
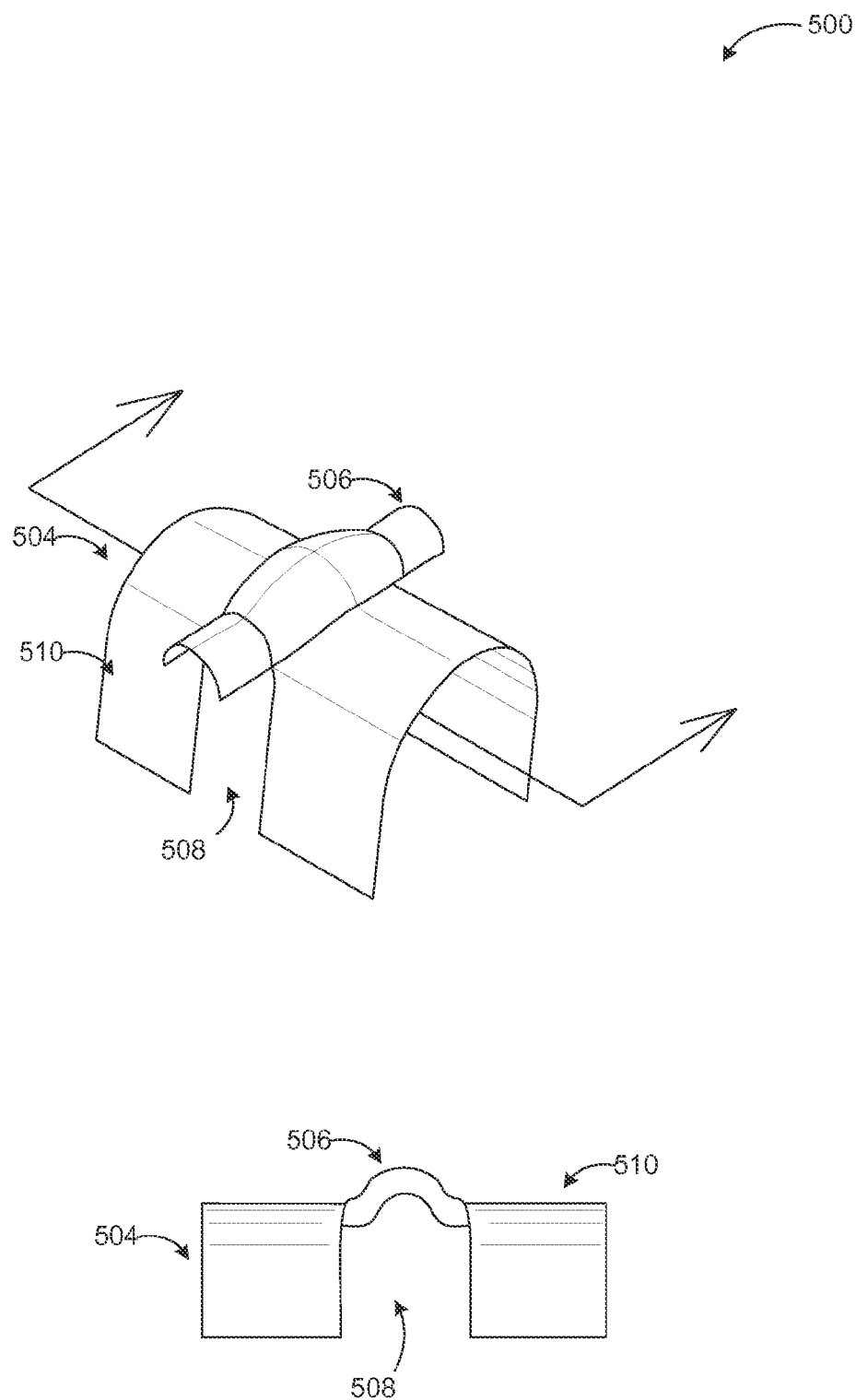
FIG. 5 illustrates a vascular reinforcement device with an embedded reinforcement structure.

FIG. 5 illustrates a vascular reinforcement device that can be placed over the left renal vein and the aorta for protecting the left renal vein from external pressures, arranged in accordance with at least some embodiments as described herein.

As previously described, the vascular reinforcement device 500 may be positioned over the aorta and the left renal vein for preventing the left renal vein from being compressed against the rigid aorta in the presence of increased abdominal pressures. A first portion 510 of the vascular reinforcement device 500 may be configured to fit over the aorta and a second portion 506 of the vascular reinforcement device may be configured to fit over the left renal vein at the position where the aorta crosses the left renal vein. The second portion 506 may be positioned substantially perpendicular to the first portion 510.

The first portion 510 may have a substantially elongated shape such that the first portion may extend over a longitudinal section of the aorta. For example, the first portion 510 may be in a range from about 2 cm to about 3 cm. Additionally, the first portion 510 may have a hollow interior 504 having an arc or semi-circular shaped cross-section such that first portion 510 may be configured to fit over, or saddle, the aorta. An average aorta may have a diameter around 2 cm, and an example diameter of the first portion 510 may be in a range from about 1.5 cm to about 3 cm.

The second portion 506 may be coupled with an upper surface of the first portion 510. The second portion 506 may also have a substantially elongated shape for extending over a length of the left renal vein, and the second portion 506 may also have a hollow interior 508 for enabling the second portion 506 to fit over the left renal vein. The second portion 506 may have a substantially semicircular cross sectional shape with a diameter in a range from about 5 mm to about 10 mm for enabling the second portion 506 to fit over the left renal vein. The hollow interior 508 of the second portion may be open and connected to the hollow interior of the first portion 510, such that the vascular reinforcement device may be placed over the aorta and the left renal vein at the location where the aorta crosses the vein, with the vein passing through the hollow interior of the second portion 506 and the aorta passing through the hollow interior of the first portion 510.

Figure 6:
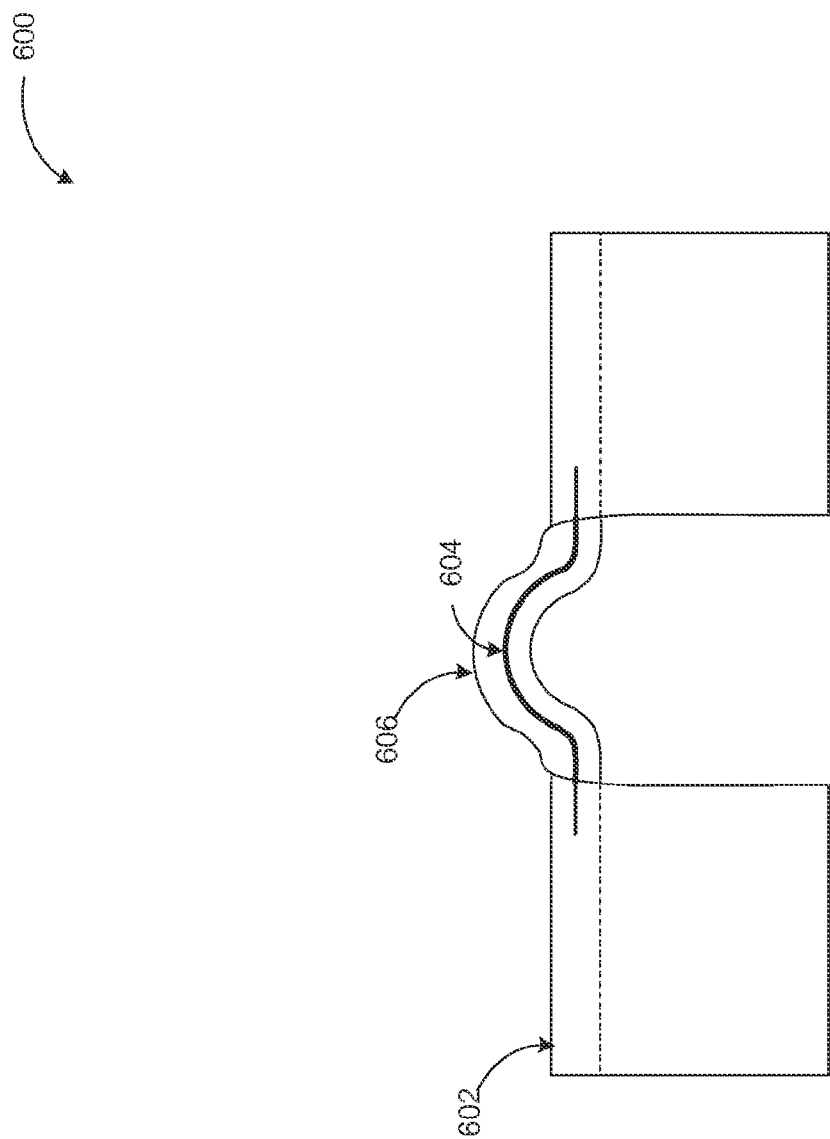
FIG. 6 illustrates placement of a vascular reinforcement device over the left renal vein where it crosses the aorta.

FIG. 6 illustrates a vascular reinforcement device with an embedded reinforcement structure, arranged in accordance with at least some embodiments as described herein. As discussed above, the vascular reinforcement device 602 may be composed of a rigid sturdy material such that when the vascular reinforcement device 602 is in position over the aorta and the left renal vein, the vascular reinforcement device 602 may prevent compression of the left renal vein against the aorta due to increased pressures within the abdomen.

In an example embodiment, the vascular reinforcement device 602 may include a reinforcement structure 604 embedded into the upper or second portion 606 of the vascular reinforcement device 602 for providing further protection from compression of the vein passing through the second portion 606. The reinforcement structure 604 may be composed of a metal such as stainless steel or nickel titanium alloy. The reinforcement structure 604 may reinforce the second portion 606 of the vascular reinforcement device 602 for enabling the vascular reinforcement device 602 to resist applied external pressures within the abdomen in a range from about 50 mmHg to about 100 mmHg.

Figure 7:
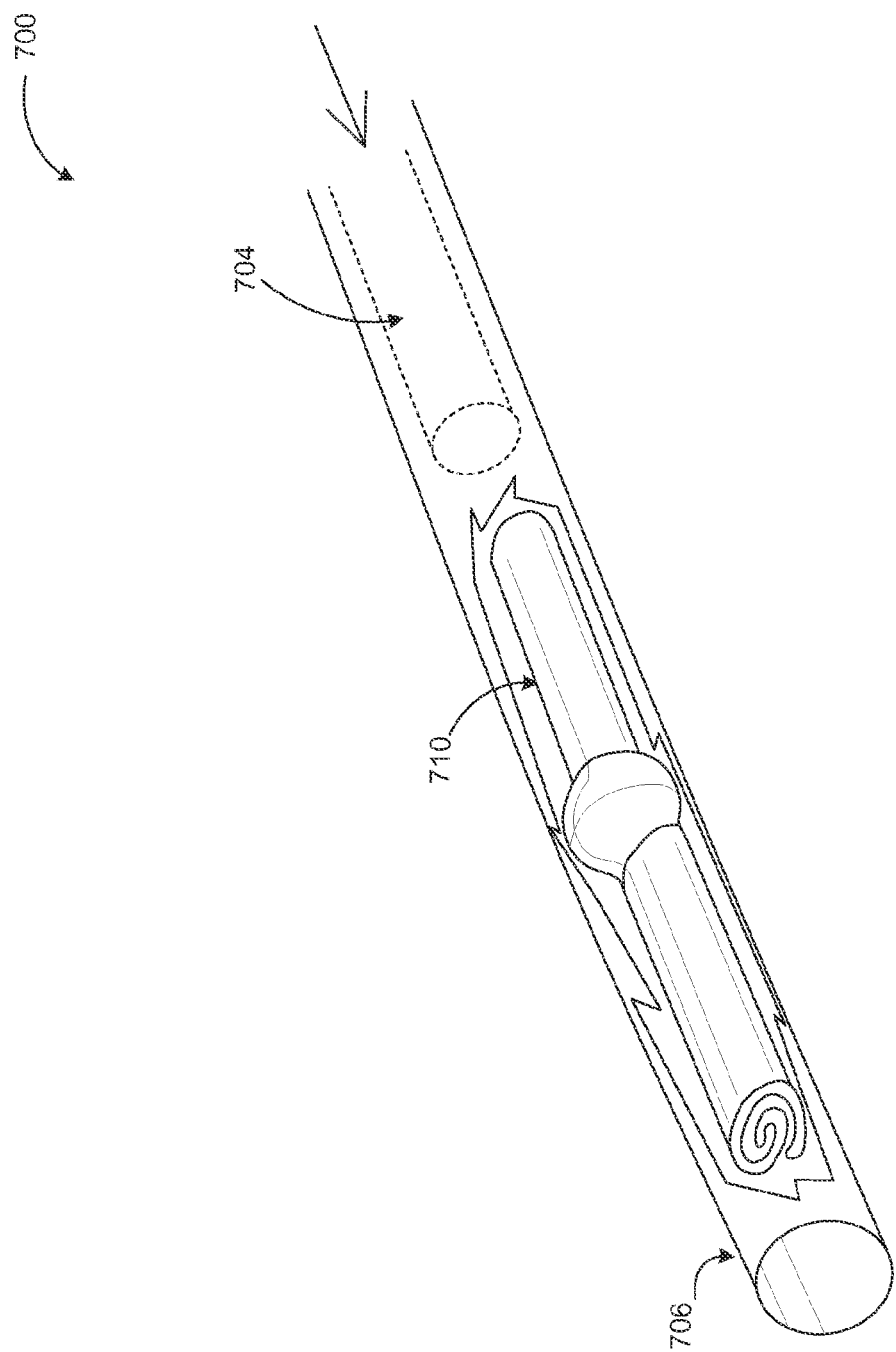
FIG. 7 illustrates delivery of a vascular reinforcement device in a reduced profile position employing laparoscopic tools, all arranged in accordance with at least some embodiments as described herein.

FIG. 7 illustrates delivery of a vascular reinforcement device in a reduced profile position employing laparoscopic tools, arranged in accordance with at least some embodiments as described herein. As illustrated in diagram 700, a vascular reinforcement device 710 may be inserted into the body and positioned over the aorta and the left renal vein in the abdominal cavity employing a laparoscopic procedure. A delivery tube 706 may provide percutaneous access to the abdominal cavity via at least one incision, and the vascular reinforcement device 710 may inserted through the delivery tube 706.

The vascular reinforcement device 710 may be configured in an initial reduced profile position for delivery to the abdominal area via the delivery tube 706. In the initial reduced profile position, the vascular reinforcement device 710 may be rolled up along a longitudinal axis of the first portion of the vascular reinforcement device, such that the vascular reinforcement device 710 in the reduced profile position forms a cylindrical shape that may fit within the delivery tube 706. The vascular reinforcement device 710 may be inserted within the delivery tube 706 in the reduced profile position, and the vascular reinforcement device 710 may be guided through the delivery tube 706 and deployed into an expanded position over the aorta and the left renal vein employing a laparoscopic guiding tool 704.

While embodiments have been discussed above using specific examples, components, and configurations, they are intended to provide a general guideline to be used for— providing a vascular reinforcement device for protecting the left renal vein from external pressures. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure describes a vascular reinforcement device for preventing compression of a vein. The vascular reinforcement device includes a first portion having a substantially elongated shape and a hollow interior, the first portion configured to saddle an aorta, and a second portion coupled with the first portion, the second portion having a substantially elongated shape and a hollow interior open and connected to the hollow interior of the first portion, the second portion configured to enable a vein to pass through the hollow interior of the second portion.

According to some examples, the first portion may have an arc-shaped cross section. The first portion may have a substantially semicircular cross sectional shape with a diameter in a range configured to fit over the aorta. The second portion may have an arc-shaped cross section configured to fit over the vein. The second portion may have a substantially semicircular cross sectional shape with a diameter in a range configured to fit over the vein. The second portion may be positioned substantially perpendicular to the first portion.

According to some examples, vascular reinforcement device may fit over the aorta and the vein at the location where the aorta crosses the vein. The vascular reinforcement device may be composed of a flexible polymer material. The polymer material may include one or more of polyamides, polyethylene, polypropylene, polyester, polyurethane, polystyrene, polysulfone and/or polyethersulfone. The vascular reinforcement device may be composed of a bio-absorbable material selected from one or more of: polyglycolic acid, polylactic acid, and polydioxanone.

According to some examples the vascular reinforcement device may include a reinforcement structure embedded into the second portion for providing further protection from compression of the vein passing through the second portion. The reinforcement structure may be composed of a metal. The metal may be one of stainless steel and nickel titanium alloy.

According to some examples, the second portion may be configured to resist an applied external pressure in a range from about 50 mmHg to about 100 mmHg. The vascular reinforcement device may be configured to be expandable from a reduced profile position to a deployed expanded position. The vascular reinforcement device may be configured to be delivered in the reduced profile position utilizing a laparoscopic procedure. The vascular reinforcement device may be configured to deploy into the expanded position over the aorta and the vein utilizing the laparoscopic procedure.

According to some examples, the present disclosure describes a method of preventing compression of a vein from external bodily tissue forces. The method may include providing a vascular reinforcement device configured to prevent external pressures from compressing a vein, the vascular reinforcement device including a first portion having a substantially elongated shape and a hollow interior configured to saddle an aorta, and a second portion coupled with the first portion, the second portion having a substantially elongated shape and a hollow interior open and connected to the hollow interior of the first portion, positioning the first portion of the vascular reinforcement device over an aorta, and enabling the vein to pass through the hollow interior of the second portion.

According to some examples, the method may also include configuring the first portion to have an arc-shaped cross section for fitting over the aorta. The method may also include configuring the second portion to have an arc-shaped cross section for fitting over the vein. The method may also include configuring the second portion to have a cross sectional diameter in a range for fitting over the vein. The method may also include positioning the second portion in a substantially perpendicular position in relation to the first portion.

According to some examples, the method may also include positioning the vascular reinforcement device over the aorta and the vein at the location where the aorta crosses the vein. The vascular reinforcement device may be composed from one or more of polyethylene, polypropylene, polyester, polyurethane, polystyrene, polysulfone and/or polyethersulfone.

According to some examples, the method may also include embedding a reinforcement structure into the second portion for providing additional protection from compression of the vein passing through the second portion. The method may also include composing the reinforcement structure from one of stainless steel and nickel titanium alloy. The method may also include configuring the second portion to resist an applied external pressure in a range from about 50 mmHg to about 100 mmHg.

According to some examples, the method may also include configuring the vascular reinforcement device to be expandable from a reduced profile position to a deployed expanded position. The method may also include delivering the vascular reinforcement device in the reduced profile position utilizing a laparoscopic procedure. The method may also include deploying the vascular reinforcement device into the expanded position over the aorta and the vein utilizing the laparoscopic procedure.

According to some examples, the present disclosure describes a system for preventing compression of a vein from external bodily tissue forces. The system may include a surgical delivery tube for providing percutaneous access to an internal area of a body via at least one incision in the skin of body, and a vascular reinforcement device including a first portion having a substantially elongated shape and a hollow interior configured to saddle an aorta, and a second portion coupled with the first portion, the second portion having a substantially elongated shape and a hollow interior open and connected to the hollow interior of the first portion, wherein the vascular reinforcement device may be configured in an initial reduced profile position for delivery to the internal area of the body via the delivery tube and deployed into an expanded position.

According to some examples, the second portion may be configured in a substantially perpendicular position in relation to the first portion. The initial reduced profile position of the vascular reinforcement device may include the first portion and the second of the vascular reinforcement portion rolled into a substantially cylindrical profile for fitting within the delivery tube. The rolled vascular reinforcement device may be guided into the internal area of the body utilizing a guiding tool.

According to some examples, the internal area of the body may be a location in the abdominal cavity near the aorta. The vascular reinforcement device may be deployed into the expanded position over the aorta and the vein. The vascular reinforcement device may be positioned over the aorta and the vein at the location where the aorta crosses the vein.

According to some examples, the vascular reinforcement device may be composed from a flexible polymer material. The polymer material may be one of polyamides, polyethylene, polypropylene, polyester, polyurethane, polystyrene, polysulfone and/or polyethersulfone. The vascular reinforcement device may be composed from a bio-absorbable material selected from one or more of polyglycolic acid, polylactic acid, and polydioxanone.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc," is used, in general such a construction is intended in the sense one having skill in the art would understand the convention (e.g., "a system having at least one of A, B, and C" would include but not be limited to systems that have A alone, B atone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as wilt be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are tier purposes of illustration and are not intended to be limiting, with the true scope and spirit being indicated by the following claims.

What is claimed is:

1. A vascular reinforcement device to prevent compression of a vein, comprising:
    a first portion having a substantially elongated shape and a hollow interior extending over a longitudinal section of an aorta, the first portion configured to saddle the aorta;
    a second portion coupled with and positioned substantially perpendicular to an upper surface of the first portion, the second portion having a substantially elongated shape and a hollow interior extending over a length of a vein, the second portion configured to enable the vein to pass through the hollow interior of the second portion;

wherein the hollow interior of the second portion is open and connected to the hollow interior of the first portion so that the vascular reinforcement device fits over the aorta and the vein at a location where the aorta crosses the vein; and a reinforcement structure embedded into the second portion, the reinforcement structure configured to provide additional protection from compression of the vein passing through the second portion against the aorta.

2. The vascular reinforcement device of claim 1, wherein the first portion has an arc-shaped cross section.

3. The vascular reinforcement device of claim 2, wherein the first portion has a substantially semicircular cross sectional shape with a diameter in a range configured to fit over the aorta.

4. The vascular reinforcement device of claim 2, wherein the second portion has an arc-shaped cross section configured to fit over the vein.

5. The vascular reinforcement device of claim 4, wherein the second portion has a substantially semicircular cross sectional shape with a diameter in a range configured to fit over the vein.

6. The vascular reinforcement device of claim 1, wherein the vascular reinforcement device is composed of a flexible polymer material.

7. The vascular reinforcement device of claim 6, wherein the polymer material includes one or more of polyamides, polyethylene, polypropylene, polyester, polyurethane, polystyrene, polysulfone and/or polyethersulfone.

8. The vascular reinforcement device of claim 1, wherein the vascular reinforcement device is composed of a bio-absorbable material selected from one or more of polyglycolic acid, polylactic acid, and polydioxanone.

9. The vascular reinforcement device of claim 1, wherein the reinforcement structure is composed of a metal that is one of stainless steel and nickel titanium alloy.

10. A method to prevent compression of a vein from external bodily tissue forces, comprising:

providing a vascular reinforcement device configured to prevent external pressures from compressing a vein, the vascular reinforcement device including:
a first portion having a substantially elongated shape and a hollow interior configured to saddle an aorta,
a second portion coupled with and positioned substantially perpendicular to an upper surface of the first portion, the second portion having a substantially elongated shape and a hollow interior configured to extend over a length of the vein,
wherein the hollow interior of the second portion is open and connected to the hollow interior of the first portion so that the vascular reinforcement device fits over the aorta and the vein at a location where the aorta crosses the vein; and
a reinforcement structure embedded into the second portion;

positioning the first portion of the vascular reinforcement device over the aorta; and enabling the vein to pass through the hollow interior of the second portion, wherein the reinforcement structure is configured to provide additional protection from compression of the vein passing through the second portion against the aorta.

11. The method of claim 10, wherein the vascular reinforcement device is composed from one or more of polyamides, polyethylene, polypropylene, polyester, polyurethane, polystyrene, polysulfone and/or polyethersulfone.

12. The method of claim 10, further comprising:
configuring the second portion to resist an applied external pressure in a range from about 50 mmHg to about 100 mmHg.

13. The method of claim 10, further comprising:
configuring the vascular reinforcement device to be expandable from a reduced profile position to a deployed expanded position.

14. The method of claim 13, further comprising:
delivering the vascular reinforcement device in the reduced profile position utilizing a laparoscopic procedure.

15. The method of claim 14, further comprising:
deploying the vascular reinforcement device into the expanded position over the aorta and the vein utilizing the laparoscopic procedure.

16. A system to prevent compression of a vein from external bodily tissue forces, comprising:

a surgical delivery tube for providing percutaneous access to an internal area of a body via at least one incision in skin of the body; and a vascular reinforcement device including:
a first portion having a substantially elongated shape and a hollow interior extending over a longitudinal section of an aorta, the first portion configured to saddle the aorta,
a second portion coupled with and positioned substantially perpendicular to an upper surface of the first portion, the second portion having a substantially elongated shape and a hollow interior extending over a length of the vein, the second portion configured to enable the vein to pass through the hollow interior of the second portion,
wherein the hollow interior of the second portion is open and connected to the hollow interior of the first portion so that the vascular reinforcement device fits over the aorta and the vein at a location where the aorta crosses the vein; and
a reinforcement structure embedded into the second portion and configured to provide additional protection from compression of the vein passing through the second portion against the aorta, wherein the vascular reinforcement device is configured in an initial reduced profile position for delivery to the internal area of the body via the delivery tube and deployed into an expanded position.

17. The system of claim 16, wherein the initial reduced profile position of the vascular reinforcement device further comprises:
the first portion and the second portion of the vascular reinforcement device rolled into a substantially cylindrical profile for fitting within the delivery tube.

18. The system of claim 17, wherein the rolled vascular reinforcement device is guided into the internal area of the body utilizing a guiding tool.

19. The system of claim 18, wherein the internal area of the body is a location in an abdominal cavity near the aorta.

* * * * *

UNITED STATES PATENT AND TRADEMARK OFFICE
CERTIFICATE OF CORRECTION

PATENT NO.          : 9,283,096 B2                              Page 1 of 1
APPLICATION NO.     : 14/129864
DATED               : March 15, 2016
INVENTOR(S)         : Adams et al.

It is certified that error appears in the above-identified patent and that said Letters Patent is hereby corrected as shown below:

Specification

In Column 1, Line 7, delete "§371" and insert -- § 371 --, therefor.

In Column 3, Line 15, delete "avascular" and insert -- a vascular --, therefor.

In Column 10, Line 19, delete "B atone," and insert -- B alone, --, therefor.

In Column 10, Line 47, delete "as wilt" and insert -- as will --, therefor.

In Column 10, Line 55, delete "tier" and insert -- for --, therefor.

Signed and Sealed this
Fifth Day of July, 2016

Michelle K. Lee
*Director of the United States Patent and Trademark Office*